US012810976B2

(12) United States Patent
Mueller et al.

(10) Patent No.: US 12,810,976 B2
(45) Date of Patent: Nov. 24, 2026

(54) SYSTEM AND METHOD FOR OPERATING AN ACTIVE MEDICAL IMPLANT

(71) Applicant: BIOTRONIK SE & Co. KG, Berlin (DE)

(72) Inventors: Jens Mueller, Berlin (DE); Thomas Doerr, Berlin (DE); Miro Selent, Nuthetal (DE)

(73) Assignee: BIOTRONIK SE & Co. KG, Berlin (DE)

( * ) Notice: Subject to any disclaimer, the term of this patent is extended or adjusted under 35 U.S.C. 154(b) by 251 days.

(21) Appl. No.: 18/714,175

(22) PCT Filed: Nov. 11, 2022

(86) PCT No.: PCT/EP2022/081623

§ 371 (c)(1),
(2) Date: May 29, 2024

(87) PCT Pub. No.: WO2023/104428

PCT Pub. Date: Jun. 15, 2023

(65) Prior Publication Data

US 2025/0037815 A1 Jan. 30, 2025

(30) Foreign Application Priority Data

Dec. 6, 2021 (EP) .................................... 21212421

(51) Int. Cl.
*G08B 1/08* (2006.01)
*A61N 1/372* (2006.01)
*G16H 10/60* (2018.01)

(52) U.S. Cl.
CPC ......... *G16H 10/60* (2018.01); *A61N 1/37217* (2013.01); *A61N 1/3727* (2013.01)

(58) Field of Classification Search
CPC .. G16H 10/60; A61N 1/37217; A61N 1/3727; A61N 1/37254; A61N 1/37252;
(Continued)

(56) References Cited

U.S. PATENT DOCUMENTS 8,271,093 B2 * 9/2012 Von Arx .......... A61M 5/14276 607/60
9,889,305 B1 * 2/2018 Hellman ........... A61N 1/37252
(Continued)

OTHER PUBLICATIONS

International Search Report (PCT/ISA/210) and Written Opinion (PCT/ISA/237) mailed Jan. 11, 2023, by the European Patent Office as the International Searching Authority for International Application No. PCT/EP2022/081623. (9 pages).

*Primary Examiner* — Tai T Nguyen
(74) *Attorney, Agent, or Firm* — Buchanan Ingersoll & Rooney PC

(57) ABSTRACT

A system for operating an active medical implant, comprising an active medical implant configured to store information related to a patient's health status in a memory of the active medical implant, wherein the active medical implant has a first short-range communication module; and a mobile terminal having a second short-range communication module configured to directly communicate with the first short-range communication module of the active medical implant via a communication link, wherein the active medical implant is configured to transmit the information related to the patient's health status to the mobile terminal via the communication link.

14 Claims, 3 Drawing Sheets

(58) Field of Classification Search
CPC .... A61B 2560/0271; A61B 2560/0276; A61B 2560/028; A61B 5/002; A61B 5/746; A61B 5/0031; H04W 4/80
USPC .................................................... 340/539.12
See application file for complete search history.

(56) References Cited

U.S. PATENT DOCUMENTS

| | | | | |
|---|---|---|---|---|
| 10,639,487 | B2 * | 5/2020 | Kivi | A61B 5/0031 |
| 11,522,919 | B2 * | 12/2022 | Yoon | H04L 63/0442 |
| 2002/0082665 | A1 | 6/2002 | Haller et al. | |
| 2005/0065815 | A1 * | 3/2005 | Mazar | A61B 5/117 600/300 |
| 2014/0273824 | A1 | 9/2014 | Fenner et al. | |
| 2015/0341785 | A1 | 11/2015 | Young et al. | |
| 2016/0330573 | A1 | 11/2016 | Masoud et al. | |
| 2018/0243573 | A1 * | 8/2018 | Yoder | H04W 4/80 |
| 2020/0094062 | A1 | 3/2020 | Yoder et al. | |
| 2020/0197711 | A1 | 6/2020 | Schilling et al. | |

* cited by examiner

SYSTEM AND METHOD FOR OPERATING AN ACTIVE MEDICAL IMPLANT

CROSS-REFERENCE TO RELATED APPLICATIONS

This application is the United States National Phase under 35 U.S.C. § 371 of PCT International Patent Application No. PCT/EP2022/081623, filed on Nov. 11, 2022, which claims the benefit of European Patent Application No. 21212421.8, filed on Dec. 6, 2021, the disclosures of which are hereby incorporated by reference herein in their entireties.

TECHNICAL FIELD

Embodiments of the present disclosure relate to a system for operating an active medical implant, a method for operating an active medical implant, and a machine-readable medium for executing the method. Embodiments of the present disclosure relate more particularly to an emergency function of an active medical implant.

BACKGROUND

Medical implants are widely used to replace, support and/or enhance biological structures of patients. Examples of medical implants include, but are not limited to, cardiovascular medical devices such as artificial hearts, artificial heart valves, implantable cardioverter-defibrillators, cardiac pacemakers, and coronary stents. Some medical implants are configured to record data, such as patient health data. However, retrieving the recorded data from the medical implant often requires specialized external equipment, Internet access, and/or trained personnel. As a result, retrieving the recorded data from the medical implant can be difficult, time consuming, and/or costly.

In light of the above, a system for operating an active medical implant, a method for operating an active medical implant, and a machine-readable medium for executing the method that overcome at least some of the problems in the art are beneficial.

The present disclosure is directed toward overcoming one or more of the above-mentioned problems, though not necessarily limited to embodiments that do.

SUMMARY

It is an object of the present disclosure to provide a system for operating an active medical implant, a method for operating an active medical implant, and a machine-readable medium for executing the method that can facilitate retrieval of data from an active medical implant, particularly in emergency situations.

At least the objects are solved by the features of the independent claims. Preferred embodiments are defined in the dependent claims.

According to an independent aspect of the present disclosure, a system for operating an active medical implant is provided. The system includes an active medical implant configured to store information related to a patient's health status in a memory of the active medical implant, wherein the active medical implant has a first short-range communication module; and a mobile terminal having a second short-range communication module configured to directly communicate with the first short-range communication module of the active medical implant via a communication link. The active medical implant is configured to transmit the information related to the patient's health status to the mobile terminal via the communication link.

According to some embodiments, which can be combined with other embodiments described herein, the mobile terminal is configured to execute an application software (App). The application software may be configured to execute at least some of the functionalities of the mobile terminal described herein, such as receiving user inputs and/or outputting information, particularly the information related to the patient's health status received from the active medical implant.

According to some embodiments, which can be combined with other embodiments described herein, the mobile terminal is configured to send an information transmission request to the active medical implant to request the transmission of the information related to the patient's health status. The active medical implant may be configured to transmit the information related to the patient's health status upon receipt of the information transmission request.

According to some embodiments, which can be combined with other embodiments described herein, the first short-range communication module and the second short-range communication module are configured for Near Field Communication (NFC) and/or Bluetooth (BLE).

According to some embodiments, which can be combined with other embodiments described herein, the first short-range communication module and the second short-range communication module are configured to establish the communication link using a pairing mode.

Preferably, a number of pairing attempts to establish the communication link is equal to, or less than, a predetermined number.

Additionally, or alternatively, a duration of the pairing mode is equal to, or less than, a predetermined duration.

According to some embodiments, which can be combined with other embodiments described herein, the first short-range communication module of the active medical implant is switchable by means of an external magnet device. The term "switchable" means that the first short-range communication module of the active medical implant can be turned on and turned off by means of the external magnet device.

According to some embodiments, which can be combined with other embodiments described herein, the active medical implant is configured to detect at least one predetermined situation related to the patient's health.

Preferably, the active medical implant is configured to store the information related to the patient's health status upon detection of the at least one predetermined situation.

Preferably, the at least one predetermined situation is selected from the group including (or consisting of) an emergency situation and a therapy situation or therapy procedure provided by the active medical implant.

According to some embodiments, which can be combined with other embodiments described herein, the information related to the patient's health status include one or more of the following:

- technical status information of the active medical implant; and/or
- medical alarms and/or technical alarms; and/or
- medical indications; and/or
- therapy parameters; and/or
- patient information; and/or
- physician information.

According to some embodiments, which can be combined with other embodiments described herein, the active medical implant is configured to encrypt the information related to the patient's health status before transmission thereof to the mobile terminal. The mobile terminal may be configured to decrypt the information related to the patient's health status which have been received from the active medical implant.

According to some embodiments, which can be combined with other embodiments described herein, the memory in which the information related to the patient's health status are stored is a dedicated memory which is logically and/or physically separate from other memories of the active medical implant.

According to some embodiments, which can be combined with other embodiments described herein, the active medical implant includes a processor module configured to control the storing of the information related to the patient's health status and/or the transmitting of the information related to the patient's health status to the mobile terminal.

Preferably, the processor module is a dedicated processor module which is logically and/or physically separate from other processor modules of the active medical implant.

According to some embodiments, which can be combined with other embodiments described herein, the communication link between the first short-range communication module and the second short-range communication module is a dedicated communication link which is logically separate from other communication links of the active medical implant.

According to some embodiments, which can be combined with other embodiments described herein, the active medical implant is configured to receive and execute at least one predefined command from the mobile terminal.

Preferably, the at least one predefined command is a command of a subset of commands executable by the active medical implant.

Preferably, the at least one predefined command is selected from the group including (or consisting of) a command to deactivate at least one therapy function of the active medical implant, a command to entirely deactivate the active medical implant, and a command to put the active medical implant in a predetermined mode of operation.

According to some embodiments, which can be combined with other embodiments described herein, the mobile terminal is selected from the group including (or consisting of) a smartphone, a personal digital assistant, a tablet, and a notebook.

Preferably, the mobile terminal is a mobile terminal of medical personnel, such as a mobile terminal of a physician.

According to another independent aspect of the present disclosure, a method for operating an active medical implant is provided. The method includes storing information related to a patient's health status in a memory of the active medical implant; sending, by a mobile terminal, an information transmission request to the active medical implant requesting a transmission of the information related to the patient's health status from the active medical implant to the mobile terminal, wherein the information transmission request is sent via a direct communication link between a first short-range communication module of the active medical implant and a second short-range communication module of the mobile terminal; and transmitting, by the active medical implant, the information related to the patient's health status to the mobile terminal via the communication link.

Embodiments are also directed at systems/devices for carrying out the disclosed methods and include system/device aspects for performing each described method aspect. These method aspects may be performed by way of hardware components, a computer programmed by appropriate software, by any combination of the two or in any other manner. Furthermore, embodiments according to the present invention are also directed at methods for operating the described device/system. It includes method aspects for carrying out every function of the device/system.

According to another independent aspect of the present disclosure, a machine-readable medium is provided. The machine-readable medium includes instructions executable by one or more processors to implement the method for operating an active medical implant of the embodiments of the present disclosure.

The (e.g., non-transitory) machine readable medium may include, for example, optical media such as CD-ROMs and digital video disks (DVDs), and semiconductor memory devices such as Electrically Programmable Read-Only Memory (EPROM), and Electrically Erasable Programmable Read-Only Memory (EEPROM). The machine-readable medium may be used to tangibly retain computer program instructions or code organized into one or more modules and written in any desired computer programming language. When executed by, for example, one or more processors such computer program code may implement one or more of the methods described herein.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

So that the manner in which the above recited features of the present disclosure can be understood in detail, a more particular description of the disclosure, briefly summarized above, may be had by reference to embodiments. The accompanying drawings relate to embodiments of the disclosure and are described in the following.

DETAILED DESCRIPTION

Reference will now be made in detail to the various embodiments of the disclosure, one or more examples of which are illustrated in the figures. Within the following description of the drawings, the same reference numbers refer to same components. Generally, only the differences with respect to individual embodiments are described. Each example is provided by way of explanation of the disclosure and is not meant as a limitation of the disclosure. Further, features illustrated or described as part of one embodiment can be used on or in conjunction with other embodiments to yield yet a further embodiment. It is intended that the description includes such modifications and variations.

Some medical implants are configured to record data, such as patient health data. However, retrieving the recorded data from the medical implant often requires specialized external equipment, Internet access, and/or trained personnel. As a result, retrieving the recorded data from the medical implant can be difficult, time consuming, and/or costly.

According to the embodiments of the present disclosure, the active medical implant stores information related to a patient's health status for later retrieval. In particular, the active medical implant may automatically generate and store emergency information for later retrieval. The mobile terminal may read the information from the active medical implant using short-range communication, such as a Near Field Communication (NFC) Standard or Bluetooth Low Energy (BLE) Standard. Optionally, the mobile terminal may perform a basic management of the active medical implant, such deactivating particular functions or even the whole active medical implant.

Accordingly, the information related to a patient's health status are easily accessible using, for example, an application (App) on the mobile terminal. In particular, the information can be accessed for instance in an emergency room by non-specialists, such as medical personnel. Accordingly, even non-specialists can detect and evaluate the condition of the active medical implant in emergency situations and optionally control/activate/deactivate basic functions such as shock delivery or therapy functions. The embodiments of the present disclosure are cost-saving, scalable, and thus applicable even in small, decentralized emergency rooms. The system of the present disclosure can be used even in areas without internet connection or 4G/5G network.

Figure 1:
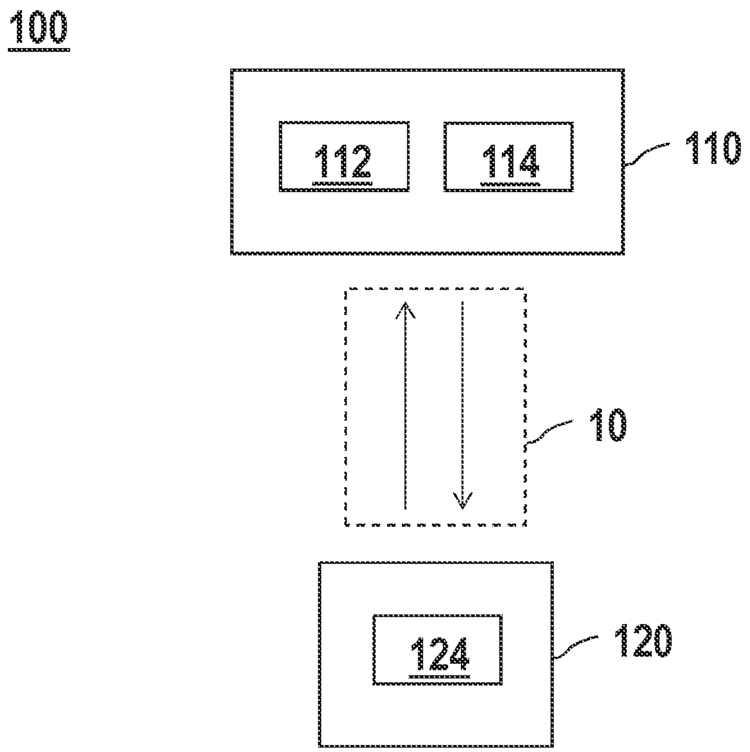
FIG. 1 shows a schematic view of a system for operating an active medical implant according to embodiments of the present disclosure.

FIG. 1 shows a schematic view of a system 100 for operating an active medical implant 110 according to embodiments of the present disclosure.

The system 100 includes an active medical implant 110 and a mobile terminal 120, such as a tablet or other mobile device. In some embodiments, the mobile terminal 120 is a mobile terminal of medical personnel, such as a mobile terminal of a physician.

The mobile terminal 120 may be configured to execute an application software (App). The application software may be configured to execute at least some of the functionalities of the mobile terminal 120 described in the following, such as receiving user inputs and/or outputting information, particularly the information related to the patient's health status received from the active medical implant 110.

The active medical implant 110 is an electronic device which is implantable or implanted in a patient's body. The active medical implant 110 may perform diagnostic and/or therapeutic functions. In some implementations, the active medical implant 110 may be a cardiovascular medical device, such as an artificial heart, an artificial heart valve, an implantable cardioverter-defibrillator, a cardiac pacemaker, or a coronary stent. However, the present disclosure is not limited thereto, and other types of active medical implants can be used to implement the principles of the present disclosure.

The active medical implant 110 has a first short-range communication module 114. The mobile terminal 120 has a second short-range communication module 124. The first short-range communication module 114 and the second short-range communication module 124 are configured to directly communicate with each other via a communication link 10. Accordingly, an offline communication between the active medical implant 110 and the mobile terminal 120 is possible because no intermediate means such as servers and/or the Internet are needed to transfer data from the active medical implant 110 to the mobile terminal 120 and vice versa.

In some embodiments, the first short-range communication module 114 and the second short-range communication module 124 can be configured for Near Field Communication (NFC) and/or Bluetooth.

Near Field Communication refers to communication protocols for low-speed communication over a short distance, such as 4 cm or less. Bluetooth is a short-range wireless technology standard for exchanging data over short distances using UHF radio waves in the ISM bands from 2.402 GHz to 2.48 GHz.

Typically, the first short-range communication module 114 and the second short-range communication module 124 are configured to establish the communication link 10 using a pairing mode. The pairing mode refers to a state of the first short-range communication module 114 and the second short-range communication module 124 when they are ready to be paired.

In some embodiments, a number of pairing attempts to establish the communication link 10 is equal to, or less than, a predetermined number. This means that the paring mode will be terminated or the pairing attempts will be aborted after reaching the predetermined number, even if the pairing was not successful. Additionally, or alternatively, a duration of the pairing mode is equal to, or less than, a predetermined duration. This means that the paring mode will be terminated or the pairing attempts will be aborted after the predetermined duration has elapsed, even if the pairing was not successful. This limitation of the pairing mode can save energy and protect a battery of the active medical implant 110.

Pairing mode is where 114 and 124 are ready to pair. The predetermined number of pairing attempts takes effect precisely in this state. The predetermined duration is not only for the paring mode but also for the paired mode (state in which 114 and 124 are connected and are no longer in pairing mode). If a connection has been successfully established, the implant must be able to actively decide after a previously configured time X whether to interrupt the connection so that the battery is not depleted.

According to some implementations, the communication link 10 between the first short-range communication module 114 and the second short-range communication module 124 is a dedicated communication link which is logically separated from other communication links of the active medical implant 110. Examples of other communication links which can be established by the active medical implant 110 with external means include, but are not limited to, communication links for programming and/or interrogating the active medical implant 110, home monitoring communication links, etc.

In some embodiments, the first short-range communication module 114 of the active medical implant 110 can be switchable by means of an external magnet device, such as a permanent magnet. Hereto, the active medical implant 110, particularly the first short-range communication module 114, may include a magnetic switch. The term "switchable" means that the first short-range communication module 114 of the active medical implant 110 can be turned on and turned off by means of the external magnet device.

Accordingly, the active medical implant 110 may only connect to the mobile terminal 120 by placing a magnet on the patient's skin in the immediate vicinity of the active medical implant 110. The magnetic switch in the active medical implant 110 activates the communication interface, i.e., the communication link 10, from the outside and puts the active medical implant 110 into pairing mode. The magnetic activation ensures that no mobile terminal connects to the active medical implant 110 unintentionally without physical contact with the patient.

The active medical implant 110 includes the memory 112 configured to store information related to a patient's health status. For example, the active medical implant 110 may be configured to automatically obtain and store the information related to the patient's health status, for instance, upon detection of at least one predetermined situation related to the patient's health.

The at least one predetermined situation may include an emergency situation, such as the occurrence of a traumatic event. Exemplary traumatic events include, but are not limited to, a fall and a car accident.

In some embodiments, the active medical implant 110 may include at least one sensor configured to detect the emergency situation, such as a fall or a car accident. In particular, the at least one sensor may be configured to provide detection data suitable to derive the emergency situation therefrom. For example, the at least one sensor may include an acceleration sensor and/or a force sensor.

Additionally, or alternatively, the at least one predetermined situation may relate to a diagnostic and/or therapeutic functionality of the active medical implant 110. For example, the recording of the information related to the patient's health status may be started in the event of syncope in bradycardia, ventricular fibrillation in tachycardia, etc.

The information related to the patient's health status, which are stored in the memory 112 upon detection of the at least one predetermined situation, may include one or more of the following:

- technical status information of the active medical implant (e.g., operating status); and/or
- medical alarms and/or technical alarms; and/or
- medical indications; and/or
- therapy parameters (e.g., stimulation mode, shock on/off); and/or
- patient information (e.g., name, date of birth, age, sex, etc.); and/or
- physician information (e.g., name or other identification of the physician).

However, the present disclosure is not limited to the above examples and the information related to the patient's health status may include other information obtainable by the active medical implant 110.

According to some embodiments, the memory 112 in which the information related to the patient's health status are stored is a dedicated memory which is logically and/or physically separate from other memories of the active medical implant 110. Examples of other memories of the active medical implant 110 include, but are not limited to, memories used in therapeutic and diagnostic functionalities of the active medical implant 110, such as memories used in a pacemaker functionality.

The mobile terminal 120 may be configured to send an information transmission request or command to the active medical implant 110 via the communication link 10 to request the transmission of the information related to the patient's health status stored in the memory 112. The active medical implant 110 may be configured to transmit the information related to the patient's health status upon receipt of the information transmission request or command from the mobile terminal 120.

In some implementations, the active medical implant 110 may be configured to encrypt the information related to the patient's health status before transmission thereof to the mobile terminal 120. For example, in addition to the security mechanisms of the Near Field Communication standard and/or Bluetooth Low Energy standard, the transmitted information is optionally protected, for example, at the business layer level by further procedures.

The active medical implant 110 may be configured to encrypt the information related to the patient's health status before the information is stored in the memory 112. In other words, encrypted information is stored in the memory 112. Alternatively, the information may be stored in the memory 112 unencrypted and may be encrypted just before the transmission of the information to the mobile terminal 120.

The mobile terminal 120 may be configured to decrypt the information related to the patient's health status which have been received from the active medical implant 110 via the communication link 10.

According to some embodiments, the active medical implant 110 includes a processor module configured to control the storing of the information related to the patient's health status and/or the transmitting of the information related to the patient's health status to the mobile terminal 120. The processor module may be a dedicated processor module which is logically and/or physically separate from other processor modules of the active medical implant 110. Examples of other processor modules of the active medical implant 110 include, but are not limited to, processor modules configured to perform therapeutic and/or diagnostic functionalities of the active medical implant 110.

Due to the separation of the process for reading out the memory 112 from the rest of the active medical implant 110, the process for reading out the memory 112 has no effect on the diagnostic and/or therapeutic function of the active medical implant 110.

According to some embodiments, the active medical implant 110 may be configured to receive and execute at least one predefined command from the mobile terminal 120. The at least one predefined command may be a command of a subset of commands executable by the active medical implant 120. In other words, only a limited number of commands is accepted by the active medical implant 110 from the mobile terminal 120. Thereby, a safety of the active medical implant 110 can be improved because it can be avoided that untrained personnel changes for instance critical settings of the active medical implant 110.

The at least one predefined command may be a command to entirely deactivate the active medical implant or a command to put the active medical implant 110 in a predetermined mode of operation. For example, the at least one predefined command may be a command to disable shock delivery (e.g., for defibrillators), a command to set the active medical implant 110 to VVI mode (e.g., right ventricular sense, stimulate, inhibit), or a command to the active medical implant 110 to 000 mode (deactivate).

According to some embodiments, which can be combined with other embodiments described herein, the mobile terminal 120 includes a user interface. The user interface of the mobile terminal 120 may include a touch user interface and/or a voice user interface. For example, the user interface may include a touch screen configured to receive a touch input from a physician. Additionally, or alternatively, the user interface may be configured to receive a voice input from the physician.

The mobile terminal 120 may be configured to output the information received from the active medical implant 110. In some embodiments, the mobile terminal 120 may control the user interface to output the received information visually, e.g., on a display and/or auditory, e.g., using a loudspeaker.

In view of the foregoing, a direct communication between the active medical implant 110 and the mobile terminal 120 to read out and manage the active medical implant 110 is used. The direct communication between the active medical implant 110 and the mobile terminal 120 is advantageous because, in order to read out and manage the active medical implant 110, it is not necessary for the data to leave a protected environment (e.g., hospital, practice, etc.), as a locally operated mobile terminal, e.g., of the clinical staff is used, and the data is also processed and displayed locally.

Figure 2:
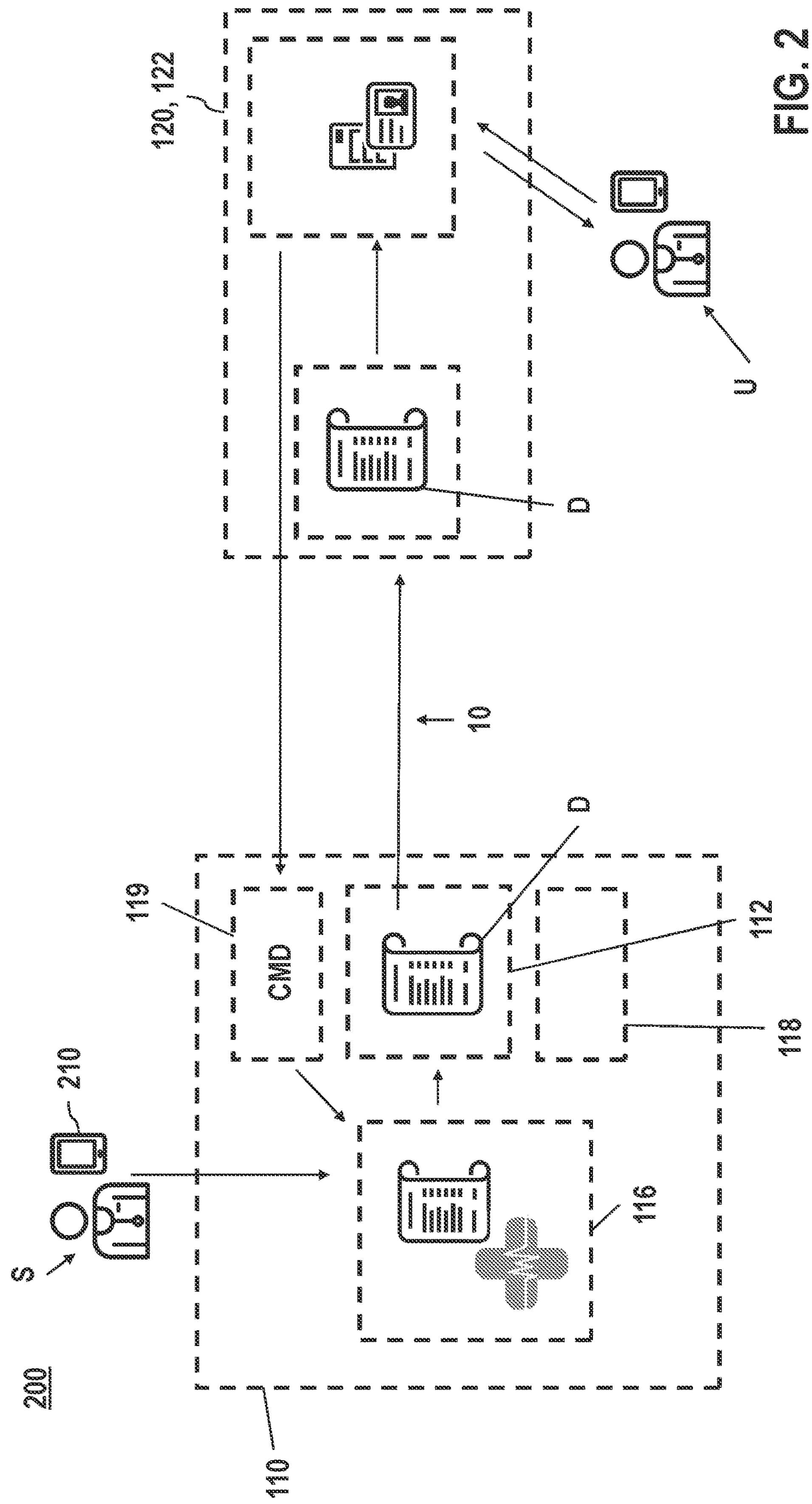
FIG. 2 shows a schematic view of a system for operating an active medical implant according to further embodiments of the present disclosure.

FIG. 2 shows a schematic view of a system 200 for operating an active medical implant 110 according to further embodiments of the present disclosure.

A specialist S may configure the active medical implant 110, e.g., during implantation thereof using a specialized external programming instance 210. The embodiments of the present disclosure, and in particular the mobile terminal, do not refer to such a configuration of the active medical implant 110 by a specialist and a specialized external programming instance 210. Instead, the embodiments of the present disclosure relate for instance to situations in which no specialist and no specialized external programming instance 210 is at hand.

The system 200 may be configured for an automatic generation of emergency information in the active medical implant 110 and the possibility of reading this emergency information later. In addition, the system 200 may be configured for a basic management of the active medical implant 110 by the mobile terminal 120, particularly an App 122 on the mobile terminal 120, using short-range communication. The reading and management may be performed in an emergency situation by non-specialists, such as medical staff in an emergency room.

The short-range communication between the active medical implant 110 and the mobile terminal 120 may implement the NFC standard or the BLE standard.

If the active medical implant 110 detects an emergency situation, the active medical implant 110 automatically stores at least some of the following information in a specially designated memory area, namely the memory 112 ("emergency memory"):

- patient information (e.g., first name, last name, date of birth)
- attending physician
- indication
- technical condition of the active medical implant
- medical and technical alarms
- therapy setting (e.g., pacing mode, shock on/off info for defibrillators)

A clinical user U can read the memory 112 from of the active medical implant 110 with the mobile terminal 120. This can be done by placing a magnet on the skin in close proximity to the active medical implant 110. The magnet activates a magnetic switch in the active medical implant 110, which signals a processing unit 118 in the active medical implant 110 to activate the short-range communication link 10.

An App 122 is locally operated on the mobile terminal 120. The App 122 establishes a connection with the active medical implant 110 via the communication link 10 and sends a command to the active medical implant 110 with the instruction to send the data D from the memory 112.

In the active medical implant 110, the memory 112, the communication link 10 and the processing module 118 for reading the memory 112 may be logically separated from the diagnostic-therapeutic part 116 (communication units and processing units are not shown).

For data transmission from the active medical implant 110 to the mobile terminal 120, the data D may be protected from data theft using, for example, symmetric encryption (e.g., AES, RC5). The App 122 decrypts and processes the queried data D locally on the mobile terminal 120 and displays the data D to the clinical user U.

In some implementations, if no data has been created and stored at the time the emergency memory 112 is queried, this can be done ad-hoc upon receipt of the command from the mobile terminal 120.

In some embodiments, the App 122 may provide a function to deactivate, e.g., a shock function and/or an entire pacing function. After selecting one of these functions, the corresponding command is sent to the active medical implant 110 and processed there. A syntactic and semantic check of the command in a separate processing module (e.g., the processing module 118 or another processing module 119) may serve as a firewall.

Figure 3:
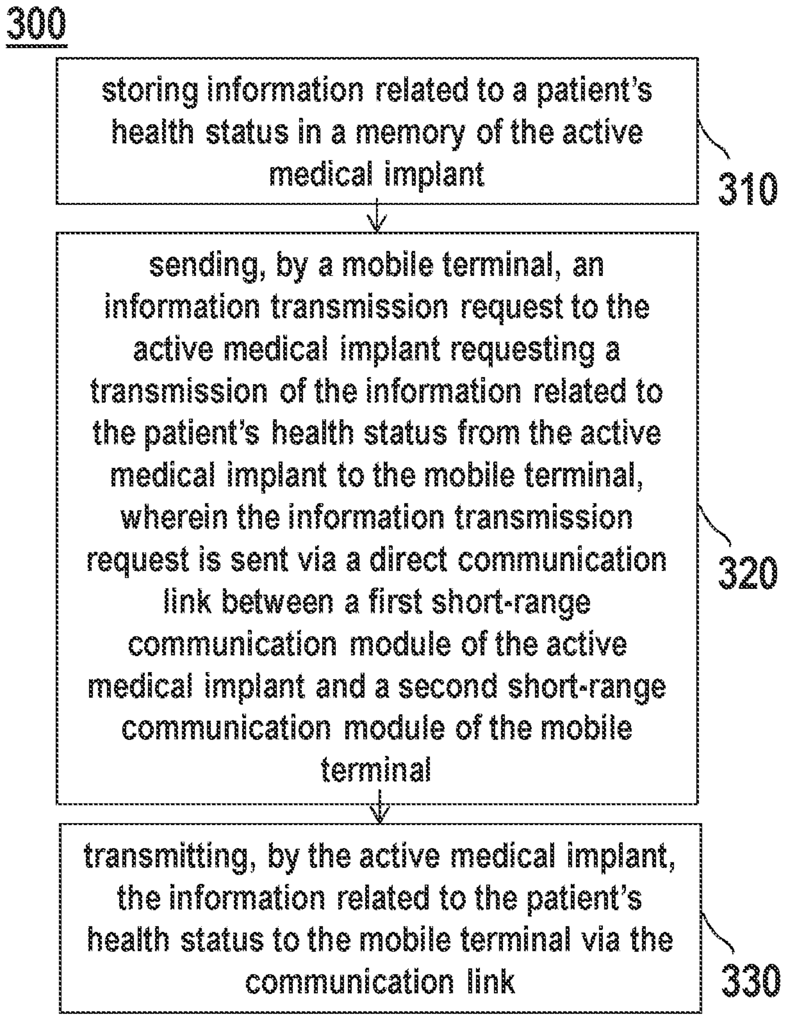
FIG. 3 shows a flowchart of a method for operating an active medical implant according to embodiments of the present disclosure.

FIG. 3 shows a flowchart of a method 300 for operating an active medical implant according to embodiments of the present disclosure.

The method 300 includes in block 310 a storing of information related to a patient's health status in a memory of the active medical implant; in block 320 a sending, by a mobile terminal, of an information transmission request to the active medical implant requesting a transmission of the information related to the patient's health status from the active medical implant to the mobile terminal, wherein the information transmission request is sent via a direct communication link between a first short-range communication module of the active medical implant and a second short-range communication module of the mobile terminal; and in block 330 a transmitting, by the active medical implant, of the information related to the patient's health status to the mobile terminal via the communication link.

According to the embodiments of the present disclosure, the active medical implant stores information related to a patient's health status for later retrieval. In particular, the active medical implant may automatically generate and store emergency information for later retrieval. The mobile terminal may read the information from the active medical implant using short-range communication, such as a Near Field Communication (NFC) Standard or Bluetooth Low Energy (BLE) Standard. Optionally, the mobile terminal may perform a basic management of the active medical implant, such deactivating particular functions or even the whole active medical implant.

Accordingly, the information related to a patient's health status are easily accessible using, for example, an application (App) on the mobile terminal. In particular, the information can be accessed for instance in an emergency room by non-specialists, such as medical personnel. Accordingly, even non-specialists can detect and evaluate the condition of the active medical implant in emergency situations and optionally deactivate basic functions such as shock delivery or therapy functions. The embodiments of the present disclosure are cost-saving, scalable, and thus applicable even in small, decentralized emergency rooms. The system of the present disclosure can be used even in areas without internet connection or 4G/5G network.

While the foregoing is directed to embodiments of the disclosure, other and further embodiments of the disclosure may be devised without departing from the basic scope thereof, and the scope thereof is determined by the claims that follow.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. A system for operating an active medical implant, comprising:

the active medical implant configured to store information related to a patient's health status in a memory of the active medical implant, wherein the active medical implant has a first short-range communication module; and a mobile terminal having a second short-range communication module configured to directly communicate with the first short-range communication module of the active medical implant via a communication link, wherein the active medical implant is configured to transmit the information related to the patient's health status to the mobile terminal via the communication link, wherein the first short-range communication module of the active medical implant is switchable by means of an external magnet device, wherein a communication interface of the first short-range communication module is activated by a detected presence of the external magnet device which places the active medical implant into pairing mode.

2. The system of claim 1, wherein the mobile terminal is configured to send an information transmission request to the active medical implant to request the transmission of the information related to the patient's health status, and wherein the active medical implant is configured to transmit the information related to the patient's health status upon receipt of the information transmission request.

3. The system of claim 1, wherein the first short-range communication module and the second short-range communication module are configured for at least one of Near Field Communication and Bluetooth.

4. The system of claim 1, wherein the first short-range communication module and the second short-range communication module are configured to establish the communication link using a pairing mode, wherein a number of pairing attempts to establish the communication link is equal to, or less than, one or more of:

a predetermined number, or a duration of the pairing mode is equal to, or less than, a predetermined duration.

5. The system of claim 1, wherein the active medical implant is configured to detect at least one predetermined situation related to the patient's health, and wherein the active medical implant is configured to store the information related to the patient's health status upon detection of the at least one predetermined situation.

6. The system of claim 1, wherein the information related to the patient's health status include one or more of the following:

technical status information of the active medical implant;

one or more of medical alarms or technical alarms;

medical indications;

therapy parameters;

patient information;

physician information.

7. The system of claim 1, wherein the active medical implant is configured to encrypt the information related to the patient's health status before transmission thereof to the mobile terminal, and wherein the mobile terminal is configured to decrypt the information related to the patient's health status which have been received from the active medical implant.

8. The system of claim 1, wherein the memory in which the information related to the patient's health status are stored is a dedicated memory which is one or more of logically or physically separate from other memories of the active medical implant.

9. The system of claim 1, wherein the active medical implant includes a processor module configured to control the storing of the information related to one or more of the patient's health status or the transmitting of the information related to the patient's health status to the mobile terminal, wherein the processor module is a dedicated processor module which is one or more of logically or physically separate from other processor modules of the active medical implant.

10. The system of claim 1, wherein the communication link between the first short-range communication module and the second short-range communication module is a dedicated communication link which is logically separate from other communication links of the active medical implant.

11. The system of claim 1, wherein active medical implant is configured to receive and execute at least one predefined command from the mobile terminal, wherein the at least one predefined command is a command of a subset of commands executable by the active medical implant, in particular wherein the at least one predefined command is selected from the group consisting of:

a command to deactivate at least one therapy function of the active medical implant;

a command to entirely deactivate the active medical implant; and a command to put the active medical implant in a predetermined mode of operation.

12. The system of claim 1, wherein the mobile terminal is selected from the group consisting of a smartphone, a personal digital assistant, a tablet, and a notebook.

13. A method for operating an active medical implant, comprising:

storing information related to a patient's health status in a memory of the active medical implant;

sending, by a mobile terminal, an information transmission request to the active medical implant requesting a transmission of the information related to the patient's health status from the active medical implant to the mobile terminal, wherein the information transmission request is sent via a direct communication link between a first short-range communication module of the active medical implant and a second short-range communication module of the mobile terminal, wherein the first short-range communication module of the active medical implant is switchable by means of an external magnet device, wherein a communication interface of the first short-range communication module is activated by a detected presence of the external magnet device which places the active medical implant into pairing mode; and transmitting, by the active medical implant, the information related to the patient's health status to the mobile terminal via the communication link.

14. A non-transitory machine-readable medium, comprising instructions executable by processors to implement the method for operating an active medical implant of claim 13.

* * * * *